United States Patent [19]
Ji et al.

[11] Patent Number: 5,888,546
[45] Date of Patent: Mar. 30, 1999

[54] EMBOLIC MATERIAL FOR ENDOVASCULAR OCCLUSION OF ABNORMAL VASCULATURE AND METHOD FOR USING THE SAME

[75] Inventors: Cheng Ji, Los Angeles; Guido Guglielmi, Santa Monica, both of Calif.

[73] Assignee: The Regents of the University of California, Oakland, Calif.

[21] Appl. No.: 519,738

[22] Filed: Aug. 28, 1995

[51] Int. Cl.$^6$ ........................................................ A61K 9/10
[52] U.S. Cl. .......................... 424/484; 424/499; 514/938; 514/952; 514/776
[58] Field of Search .................................... 424/424, 484, 424/499; 514/938, 952, 776

[56] References Cited

PUBLICATIONS

Sheffel et al., "Albumin Microspheres for Study of the Reticuloendothelial System," J. Nuclear Medicine, v. 13, n. 7, pp. 498–503, Jul. 1972.

Sugibayashi et al., "Drug–carrier Prop. of Albumin Microspheres in Chemo. II. Prep & Tissue dist. in Mice of Microsphere–entrapped 5–Fluoracil," Chem. Pharm. Bull. 27 (1), 204–09, 1979.

goldberg, et al., "Biodeg. of albumin Microspheres used for Regional Chemo. in patients w/Colorectal Liver Metaphases," Nuclear Medicine Comm., v. 12, n1, 57–63, 1991.

Kyptani et al., "Study of Embol. Mat. for Chemo–embol. Ther. of Hepatocellular Carcinoma. Antitumor Eff. of cis-–Diamm. Albumin Micro.," Chem. Pharm. Bull., 40 (10), 2814–16, 1992.

Czejka et al., "Pharmacokinetics of Mytomycin C in Patents after Bolus inj. & Chemo. of the Hepatic Artery w/spherex starch party.," Eur. j. Drug Metab. & Pharm. 17 (2), 85–87, 1992.

Egbaria et al., "Adsorption of Fluorescein Dyes on Albumin Microspheres," Pharmaceutical Research, v9, n5, 629–35, 1992.

Sasaki et al., "Tetracycline admin. Inc. Collagen Synth. in Osteobbsts of streptozotocin–Induced Diacetic Rats: A Quant. Autor. study," Calcif. tissue Int. 50:411–419, 1992.

Sankari et al., "Sclerotherapy w/Tetracycline for Hydroceles in Renal Transplant Patients," J. of Urology, v. 148, 1188–1189, 1992.

Kan et al., "Distr. & Effect of Iodized Poppyseed Oil in Liver after Hepatic Artery Embol.: Exp'tal study in Several Animal Species," Radiology, v186, n.3, 861–866, 1993.

Luo, "Treatment of hepatocellular Carcinoma by Transarterial Approach," Chinese Medical Journal, v73, n3, 158–160, 1993.

Cheng et al., "Study on Cisplatin albumin Microspheres for Neck Ext. Artery Embol.," Acta Pharmaceutica Sinica, v28, n8, 604–8, 1993.

Hettler et al., "Polyhydroxamic Microcapsules Prepared from Proteins :a Novel Type of Cheating Microcapsules," J. Microencapsulation, v11, n2, 213–224, 1994.

Benita et al., "Biodegradable cross–linked Albumin Microcapsules for Embolization," J. of Microencapsulation, v1, n4, 317–327, 1984.

Nicholson et al., "Thrombin–Soaked Embolization Coils : the Effect of Whole Blood Clotting time," Clinical Radiology, 46, pp. 108–110, 1992.

Alexander et al., "History of Endovoscular Therapy," Neurosurgery Clinics of N. America, v 5, n 3, pp. 383–391, 1994.

Khayata et al., "Materials & Embolicc Agents for Endovascular Treatment," Neurosurgery Clinics of N. America, v 5, n 3, pp. 475–484, 1994.

fournier et al., "Endovas, Treatment of Intracerebral Arteriovenous Malformations: Exp. in 49 cases," J. of Neurosurgery, v 75, n 2, pp. 228–233, 1991.

Ichida et al., "Therapeutic Effect of a CDDP–Epirubicin-–Lipiodol Emulsion on Advanced Hepatocellular Carcinoma," Cancer Chemo. & Pharmacology, 33 suppl., 574–8, 1994.

*Primary Examiner*—Thurman K. Page
*Attorney, Agent, or Firm*—Daniel L. Dawes

[57] ABSTRACT

A multipurpose ointment (MPOc) in a semisolid-semiliquid form and a multipurpose particle (MPPc) in a solid soft particulate form are prepared by combining a matrix base in a aqueous solution with a liquid oil base and added modifiers and medications to form either an ointment or suspension of particles for endovascular disposition for embolizing abnormal microvascular beds or nidi. The ointment or particles are formed from a albumin (human serum or chicken egg) matrix or equivalent material or combination of the same in an aqueous solution, typically contrast-medium solution, which has been emulsified with a radiopaque oil base such as ETHIODOL, and then heated to modify the mobility, viscosity, deformability, elasticity, surface tension and friction along with the inclusion of medications and modifiers for the desired physical characteristics and biological end effects.

17 Claims, No Drawings

EMBOLIC MATERIAL FOR ENDOVASCULAR OCCLUSION OF ABNORMAL VASCULATURE AND METHOD FOR USING THE SAME

BACKGROUND OF THE INVENTION

1. Field of the Invention

The invention relates to the field of endovascular embolic materials for embolization in abnormal microvascular beds or nidi, and in particular to a semisolid-semiliquid endovascular embolic multipurpose ointment and a corresponding soft particle form of embolic beads.

2 Description of the Prior Art

Endovascular embolic materials, which are currently used for embolization of abnormal microvascular beds or nidi, include injectable solid particles, sutures, fibers, tissue or sponge fragments, as well as liquid agents such as glues and emulsions. In the case of brain arteriovenous malformation embolization, almost all of the solid embolic materials are nonradiopaque. Most of these materials are biodegradable, for example Avitene fibers, sponge and dura fragments, protein microbeads and the like, which offer only temporary embolization. See Lon F. Alexander et al., *"The History of Endovascular Therapy,"* Neurosurgery Clinics of North America, 5 (3) at 383–391 (1994). The nondegradable materials, such as polyvinyl alcohol (PVA) particles, silk sutures and the like, have a high rate of recanalization and collateralization, that is a tendency to reopen vessels and provide parallel vessel paths, not withstanding that these materials may permanently remain at the embolized sites.

It is believed that the spontaneous thrombolysis and angiogenesis are the main contributing mechanisms to this recanalization and collateralization. Furthermore, these prior art types of solid materials usually tend to stay proximate to the injection site instead of moving to the nidus itself due to the poor deformability of these materials. As a result, a considerable number of nidus vessels remain anatomically open even though the whole arteriovenous malformation nidus is angiographically occluded. These remaining portions, which lack embolic material, offer beds for recurrence. See for example Mazen H. Khayata et al., *"Materials and Embolic Agents for Endovascular Treatment,"* Neurosurgery Clinics of North America, 5 (3) at 475–84 (1994).

Currently used liquid embolic materials are usually radiopaque, because they are usually mixed with Lipiodol and/or tantalum powder. For example, while liquid glue, such as isobutyl-2-cyanoarylate (IBCA) has a good mobility rate inside the delivery microcatheter, it is unpredictable inside the nidus due to difficulties in controlling its solidification rate. An optimal result may be achieved if a glue with suitable adjusted solidification time is delivered into the desired dominant portion of the arteriovenous malformation nidus. However, further treatment, such as surgical removal or radiation, is usually required in most cases using liquid materials. See Fournier et al., *"Endovascular Treatment of Intracerebral Arteiovenous Malformations: Experience in 49 Cases,"* Journal of Neurosurgery, 75 (2) at 228–33 (1991).

The nonsolidifiable liquid material, such as Lipiodol emulsion, cannot be applied in the treatment of arteriovenous malformation because the emulsion would be washed away within minutes.

In the case of malignant tumor endovascular treatments, such as hepatocellular carcinoma embolizations, the liquid emulsions made of Lipiodol and aqueous anticarcinogenic solutions show much better effects than most solid drug carrier particles. This is because the liquid emulsions have better mobility and can embolize malignant microvascular beds more extensively than solid particles. In addition, the emulsion can carry more anticarcinogens into the tumor. See Ichida et al., "Therapeutic Effect of a CDDP-Epiiubicin-Lipiodol Emulsion on Advanced Hepatocellular Carcinoma," Cancer Chemotherapy and Pharmacology, 33 suppl., S74-8 (1994). However, liquid emulsions have less friction in the embolized microvascular beds, such that in some high blood flow tumors, especially those with intratumoral microshuntings similar to the arteriovenous malformation nidi, the delivered embolic agent can be washed away within hours or days. See Kan et al., *"Distribution and Effect of Iodized Poppyseed Oil in the Liver After Hepatic Artery Embolication: Experimental Stucly in Several Animal Species,"* Radiology, 186 (3), at 861–6 (1993); and Luo "Approach," Chung-Hua i Hsueh Tsa Chih Chinese Medical Journal, 73 (3) at 158–60, 191 (1993).

What is needed in this case is a more stable embolic carrier with a better relative friction and mobility to produce a longer lasting embolization and to maintain a higher drug concentration within the target tumors.

Therefore in general what is needed is an improved therapeutic result in endovascular embolizations which is not subject to the disadvantages discussed above in connection with each of the prior art embolic materials.

BRIEF DESCRIPTION OF THE INVENTION

The invention is an endovascular embolic composition. The embolic composition comprises an aqueous solution of a matrix base having a sponge-like structure for providing self-lubrication and surface hydration. A liquid oil base is mixed with the aqueous solution of the matrix base to form an emulsion for endovascular disposition for embolization in abnormal microvascular beds or nidi. The matrix base is comprised of albumin or its equivalents (e.g. proteins or polymers other kinds of which can jelly the emulsion as a whole) dissolved in an aqueous solution (e.g. a contrast-medium solution or its equivalents such as water, buffer solutions and the like). The aqueous solution of the matrix base is mixed and emulsified with the liquid oil base in a volume ratio ranging between 1-to-1 to 1-to-5 respectively. In the illustrated embodiment the liquid oil base is a Ethiodol solution.

The emulsion is heated in a water bath at a temperature of 50 degrees to 100 degrees centigrade according to final physical characteristics of the embolic composition desired.

The embolic composition may further comprise radiopaque materials, such as radiopaque materials selected from the group comprising powders of metrizamide, tantalum, tungsten and combinations of the same.

Additional embodiments of the embolic composition further comprise or include medicants, such as medicants selected from the group comprising hemostatics, positive electrical char(,e donators, sclerosants, anticarcinogens, radioactive agents and combinations of the same.

Other embodiments of the embolic composition may further comprise liposoluable modifiers, such as phospholipids, water soluble modifiers such as polyethylene glycol, and stabilizing agents such as ascorbic acid (vitamin C).

In one particle form of the embolic agent the aqueous solution of the matrix base and liquid oil base are emulsified and formed into particles of a predetermined size range. The particles then are suspended in a liquid medium. In another form of the embolic composition the aqueous solution of the matrix base and liquid oil base are formed into a homogeneous semiliquid-semisolid ointment.

The invention is also a method of preparing an endovascular embolic composition comprising the steps of dissolving a matrix base into an aqueous solution. The dissolved matrix base is mixed with a liquid oil base in a volume ratio in the range of approximately 1-to-1 to 1-to-5 of the aqueous solution of the matrix base to the liquid oil base. An emulsion is produced from the mixture of the liquid oil base in the dissolved matrix base. The emulsion is heated for a predetermined period of time to define a selected physical characteristic thereof. After heating, the matrix base within the emulsion can form a sponge-like structure for providing self-lubrication and surface hydration. The method may further comprise adding medications or modifiers to the aqueous solution prior to mixing with the liquid oil base.

In one embodiment the method further comprises forming particles from the heated emulsion by quick cooling the emulsion as it is expressed from a needle into a liquid, collecting the particles by filtration, and suspending the particles in a liquid medium such as normal saline.

The invention and its various embodiments may be better understood by now turning to the following detailed description.

DETAILED INVENTION OF THE PREFERRED EMBODIMENTS

A multipurpose ointment (MPOc) in a semisolid-semiliquid form and a multipurpose particle (MPPc) in a solid soft particulate form are prepared by combining a matrix base in a aqueous solution with a liquid oil base and added modifiers and medications to form either an ointment or suspension of particles for endovascular embolization of abnormal microvascular beds or nidi. The ointment or particles are formed from a human serum or chicken egg albumin or its equivalent matrix in an aqueous solution which has been emulsified with iodized oil and then heated to modify the mobility, viscosity, deformability, elasticity, surface tension and friction along with the inclusion of medications and modifiers for the desired physical characteristics and biological end effects.

The illustrated embodiment describes two multifunctional materials used as improved therapeutic embolic materials. The first, which shall be labelled in the specification as a multipurpose ointment, MPOc, is in semisolid-semiliquid form. The second, which shall be described as a multipurpose particle, MPPc, is in a solid/soft particulate form. Both forms not only compactly fill most of the arteriovenous malformation nidus, but also inhibit angiogenesis and promote thrombogenesis as well as thrombus organization, thereby minimizing the anatomically empty portion of the treated vascular system. Therefore, what is produced is a more complete and longer lasting embolization, which is more likely to lead to a permanent cure for the arteriovenous malformation. In the case of high flow vascular tumor embolization, both forms will offer a more complete and longer lasting chemoembolization than conventional embolic materials.

Consider first the multipurpose ointment, MPOc, and its clinical applicability. The endovascular multipurpose ointment is a family of ointment-like, highly radiopaque embolic materials. A common component of this family of embolic agents act like a multipurpose vehicle which can carry different medications and be delivered to target lesions throughout interventional devices, including but not limited to direct puncture needles, drainage tubes, endovascular catheters, and any type of delivery instrument now known or later devised.

Like most topical ointments which are presently used clinically, the multipurpose ointment contains two components, namely a matrix base and a liquid oil base. The ointment is in a semisolid-semiliquid form. However, the matrix base can form an exclusive sponge-like structure which give the multipurpose ointment two unique characteristics: (1) self-lubrication when disposed inside a delivery device such as a needle or catheter; and (2) surface hydration when disposed inside blood vessels or other site within the vascular system. With these two unique characteristics, in addition to suitable mobility, viscosity, interfacial tension and friction, the multipurpose ointments can pass through the smallest internal diameter needles and microcatheters with ease, and yet still offer maximum and stable embolization.

Once a medication is encapsulated within the multipurpose ointment, it is slowly released for a predetermined period of time, typically for several weeks from the multipurpose ointment embolic to cause its local effects with minimal or no systemic side effects. The multipurpose ointment eventually is metabolized and leaves an organized lesion.

The further functions of the multipurpose ointment, other than mechanical blockage, depends on the added medications. For example, a first multipurpose ointment, here labelled as MPO1, is made by adding tetracycline, a common sclerosant, to the generic multipurpose ointment described above. MPO1, therefore, causes organization processes of the treated nidus leading to permanent occlusion.

A second multipurpose ointment, labelled here as MPO2, contains thrombin, which is commonly used as an enzymatic hemostatic to promote local thrombogenesis inside the nidus. This may result in embolizing a multifeeder arteriovenous malformation through the main feeder only.

The other members of the multipurpose ointment family may contain different sclerosants, anticarcinogens, radioactive agents, antibiotics, electrical charges and biological agents of any kind now known or later discovered, including combinations of these agents. Therefore, the family of multipurpose ointments can be widely applied as embolic materials for tumors, arteriovenous malformations, varicose veins, cysts, bleeding vessels and any other endovascular disease or condition to which an embolism may be relevant.

In order to embolize arteriovenous fistula, or aneurysm, the multipurpose ointment may be applied in conjunction with other endovascular embolic materials, devices or methods, such as balloons and coils. The uses or range of the corresponding multipurpose particles, MPP, is to embolize bleeding vessels, tumors, or arterio-veneous malformations.

The application of the multipurpose ointment, MPOc, now having been described, turn its composition. The first of the two basic parts of the multipurpose ointment is the matrix base and aqueous solution. The matrix base, may be comprised of albumin, human serum or chicken egg or its equivalents, which is a nonantigenic, biodegradable and biocompatible material, and which is already widely used and available clinically as a matrix material in microspheres and microcapsules. Some of these microspheres, in fact, were originally designed for use in endovascular chemoembolizations.

There are some equivalent materials which could replace or mix with the albumin to form the matrix base. These materials should have the following two properties as of albumin: (1) soluability in aqueous solutions; and (2) the ability to coagulate or solidify with the aqueous solution to form a sponge-like matrix after certain heating or certain physical treatment. Such materials include collagen, globular protein, fibronectin, laminin and the like proteins or polymers now known or later discovered.

The aqueous solution of the first basic part of the multipurposed ointment functions as a solvent to dissolve the matrix base (e.g. albumin and the like). This aqueous solution typically is, but is not limited to, contrast-medium solutions, such as OMNIPAQUE manufactured by Sterling Pharmaceuticals, Inc. Sterile water, normal saline, buffer solutions and all similar solutions now known or later discovered could function as the solvent of the matrix base.

The second basic part of the multipurpose ointment, the liquid oil base, is comprised of OMNIPAUE manufactured by Sterling Pharmaceutical Inc. of Puerto Rico, iodized oil, such as ETHIODOL as manufactured by Savage Laboratories, a division of Atlanta Inc. of Melville, N.Y. OMNIPAQUE and ETHIODOL are two kinds of contrast agents widely used clinically for angiography and lymphography, respectively.

In addition to these two basic elements, the multipurpose ointment may include optional agents to modify the mobility, viscosity, deformability, elasticity, surface tension and friction of the multipurpose ointment generically. Therefore, the following optional materials may be added, all of which are nontoxic, nonantigenic and biocompatible:

a. Liposoluble modifiers, for example cholesterol, bone wax, phospholipids, mixed with Ethiodol;
  b. water-soluble modifiers, for example polyethylene glycol, povidone, dextran, starch, chitin, chitosan, gelatin, alginate, DNA and the like, can be dissolved in aqueous albumin solutions;
  c. surfactants, emulsifiers and cross-linking agents and stabilizing agents such as vitamin C can also be added to provide a stable mixture; and
  d. radiopaque material, such as powders of metrizamide, tantalum or tungsten to enhance fluoroscopy visibility of the multipurpose ointments.

This listing is illustrative only and is not intended to limit the scope of the present invention which includes all modifiers now known or later devised.

Examples of the medication which may be added as optional materials include, but are not limited to:

a. hemostatics, such as thrombin and the like;
  b. positive electrical charge donators, such as stearylamine and the like, used for promoting thrombogenesis;
  c. sclerosants, such as tetracycline, deoxycycline and the like, for sclerosing the embolized vessels;
  d. radioactive materials, such as iodine 131 labelled Lipiodol, P-32 colloid, Y-90 powders and the like, used for internal radiation therapy to control both angiogenesis and proliferation of malignant cells.
  e. anticarcinogens, such as cis-platinum, adriamycin and the like for killing malignant cells.

This listing is illustrative only and is not intended to limit the scope of the present invention which includes all medications now known or later devised.

Medications delivered with the multipurpose ointments are intended for their own original or unique purposes apart from embolization. The local effects of these agents is increased at the delivery site by virtually their proximity, while their toxicity to the overall system is decreased.

The application and the composition of the multipurpose ointment now having been described, consider one method by which the ointment may be prepared. The albumin or its equivalent is dissolved into an aqueous contrast-medium solution. For example, 50 to 400 milligrams of the albumin can be dissolved per cubic centimeter of the contrast-medium solution. Medications and modifiers may then be added after the albumin is in solution. The aqueous solution is then mixed with Lipiodol at the rate of 1-to-1 to 1-to-5 in volume ratios respectively. This mixture is then completely emulsified in the mixing process. The emulsion is heated in a water bath to a temperature approximately in the range of 50 degrees to 100 degrees centigrade.

The final product is comprised of multipurpose ointment with the precise preparation parameters being chosen in order to obtain the desired deformability, elasticity, viscosity, as well as self-lubrication and surface hydration. The concentration of albumin, the degree of emulsification, and the degree and duration of heating significantly change the desired physical characteristics of the multipurpose ointment and, therefore, are manipulated according to the end characteristics desired in any given application.

An Example of MPO1

Preparation of MPO1, which is an embolizing agent for arteriovenous malformation in the brain, contains the basic multipurpose ointment composition with functional medications, such as sclerosing agents tetracycline and its analog deoxycycline. MPO1 is improved over conventional embolic materials in that it is: (1) highly radiopaque and clearly visible under X-ray fluoroscopy; (2) very controllable when delivered through a microcatheter; (3) effective for permanent occlusion or sclerosing of the vessel lumens by means of metabolizing and organizing MPO1; and (4) safe, since the chemically induced inflammatory reaction by MPO1 can only be found within the vessel lumens for a very short period of time.

In this example, 150 milligrams of albumin from chicken egg, grade V, manufactured by Sigma Chemical Company of St. Louis, Mo., and 250 milligrams of tetracycline hydrochloride are dissolved in 1 milliliter of Omnipaque which provides the aqueous contrast-medium. The solution is blended and emulsified with Ethiodol until the total volume reaches 5 milliliters. The final mixture is then heated at approximately 58 degrees centigrade in a water bath for 10 minutes. The MPO1 is prepared under aseptic conditions and then stored at 4 degrees centigrade.

Consider now a test of the physical characteristics of MPO1 prepared as described above in the example. Each milliliter of MPO1, thus contains 30 milligrams of albumin, 50 milligrams of tetracycline, 0.2 milliliters of Onmipaque and 0.8 millimeters of Ethiodol. The MPO1 was injected through a number 25 needle into a small cup with normal saline for evaluating its dissolvability in water. To test the friction between MPO1 and the microcatheters, 0.2 milliliters of MPO1 was injected into a Tracker 18 catheter using normal saline or 20 percent fat emulsion to push the MPO1 through the catheter. The pressure required to push the MPO1 out of the catheter was recorded. The same test was repeated with a Tracker 10, manufactured by Target Therapeutics Inc. of San Jose, California, and Magic 1.8 and Magic 1.5 catheters, manufactured by Balt of Montmorency, France. The test was also repeated after MPO1 was stored under 4 degrees centigrade for 1, 2, 3 and 4 months in sequence.

The friction test show that the pressure required for pushing 0.2 milliliters of MPO1 with normal saline through a Tracker 18 microcatheter is always below 70 psi and less than 100 psi for a Tracker 10, 120 psi for a Magic 1.8, and 150 psi for a Magic 1.5. When the test is repeated with 0.1 milliliters of MPO1 for a Magic 1.8, the pressure is less than 80 psi, and less than 110 psi for a Magic 1.5. When a 20 percent fat emulsion instead of saline is used to push the ointment through the catheter, the pressure is reduced about 20 percent, for example, 65 psi for a Magic 1.8 and 90 psi for a Magic 1.5. The same test repeated for MPO1 stored for up to four months shows the same results.

The in vitro evaluation disclosed that MPO1 is undissolvable in normal saline. Shortly after it is injected in the saline, the surface becomes white and swollen due to hydration on the surface. After three months of storage, however, its color begins to change from bright yellow to brown which is believed to be due to decomposition of the tetracycline. No changes were found in MPOc.

MPO1 has the characteristics of both solid and liquid materials. The degree of solidity allows MPO1 to occlude small vessels. Furthermore, the surface hydration increases the friction between the vessel intima and MPO1, which helps to block the vessels. Liquidity as well as its self-lubrication makes MPO1 easier to be injected through microcatheters.

It is know that hand injection with a one cc syringe can easily reach pressures of 400 psi. The rupture pressure for Tracker catheters is designed at about 500 psi. However, the rupture pressure for the Magic system or flow-direct microcatheters is about 200 psi and the recommended injection pressure is not to exceed 100 psi. Giving these restrictions and the results of the friction test, the use of higher pressure catheters is recommended in connection with MPO1 and special attention should be paid to reduction of the pushing pressure, such as by inclusion of the 20 percent fat emulsion.

Consider now an in vivo test of MPO1 prepared as described in the example above. Ten swine weighing 50 to 60 pounds of mixed sexes were used for the in vivo study. Pigs 1–6 underwent embolization of rete and the ascending cervical artery using MPO1. Pigs 7 and 8 underwent embolization of lung and rete with MPO1, and the ascending cervical artery with the generic multipurpose ointment. Pigs 9 and 10 underwent bilateral rete embolization with conventional PVA particles as a control. Angiographies were performed just before and immediately after the embolizations and followed up at one and two weeks, one, two, three and six-month intervals thereafter. Pig 1 was sacrificed on the first day, pig 2 at two weeks after embolization, pigs 3, 4 and 7 at two months, pig 8 at three months, pigs 5, 6, 9 and 10 at six months. All vessels and lungs which were embolized were harvested for pathological study. Samples of spleen and lymph nodes were collected for histological study and all other organs were subjected to gross examination.

In the swine, no recanalization, that is reopening of the feeding arteries, was found angiographically for up to six months in the MPO1 group. However, recanalization occurred in all the conventional PVA embolized retes. The degree of feeding artery reopening is between 20 and 80 percent and tends to increase with time. A normal rete is fed mainly by the ascending pharyngeal artery and also is partially supplied by a small branch from the middle meningeal artery. This small feeder acts like a collateral artery. After the main feeder pharyngeal artery and the rete is embolized with conventional PVA particles, the immediate post embolization angiographies show that 20 to 35 percent of the rete microvesculatures remain patent or unembolized, which obtain blood supply from the collateral branch. However, the group treated by MPO1, only zero to ten percent of the rete remain open. Follow-up angiographies of the conventional PVA group show the middle meningeal branch enlarges with time and its feeding portion of the rete extends into the previously embolized portion. The percentage of the patent vessels in the rete increases up to 50 to 70 percent. However, in the MPO1 group, follow-up angiographies show no change or even smaller changes in size of the collateral branch and its domain.

No recanalization is found in ascending cervical arteries embolized with MPO1, but the arteries embolized with MPOc all reopen completely within two weeks.

All swine included in the study were healthy until sacrificed and no abnormal behaviors were found. Two of the pigs underwent pulmonary artery embolization with MPO1. One was embolized into a surgically constructed arteriovenous fistula. The other was embolized directed into pulmonary arteries via venous approach. The total amount of MPO1 for each animal was 1.0 milliliters with follow-up chest radiographies showing normal findings.

After sacrifice, the brain, liver, spleen and kidney were grossly examined. No infarctions or inflammations were found. Several small congested infarctions of approximately 0.5 to 1.0 centimeter were found in the lungs which underwent pulmonary artery embolization. Approximately 95 percent of the lung volume was intact.

Embolized retes and ascending cervical arteries appeared harder than unembolized vessels. The adventitia appeared normal and no adhesion or edema were found in surrounding tissues.

The histopathological studies indicated that the vascular lumps from the size of 50 microns to 2.0 millimeters were filled homogeneously with MPO1. At the same day of embolization, no signs of inflammatory reaction were found. Two weeks after embolization, chronic inflammatory response was seen inside the vessel lumens. Macrophages and lymphocytes infiltrated into the MPO1. Granulation tissue instead of MPO1 filled out the whole lumen of microvessels which were less than 300 microns in diameter. In small (300 micron to 1.0 millimeter) and in middle sized (1.0 to 2.0 millimeter) vessels, MPO1 remained in the center of the lumens and the granulation tissue extended from the vessel wall into the MPO1.

Two months after embolization, fibroblasts and collagen fibers instead of macrophages became the dominant elements filling the vessel lumens. In microvessel lumens, matured scar tissue formed. However, granulation tissue can be seen in small vessels and some chronic inflammatory cells remained in the lumen center. Some MPO1 still remained in the center of some of the larger vessels.

At six months after embolization, also most all vessel lumens were filled with scar tissue. MPO1 could only be traced in one or very large vessels.

Fluorescent microscopic examination confirmed that the vessel walls were intact. The internal elastic laminas were preserved. At two weeks after embolization, the minimum amount of chronic inflammatory cells was found infiltrating the vessel walls including the advantitias. However, the phenomenon disappeared at two months and there was no necrosis or other damage.

MPO1 may be sterilized by any means now known or later devised with the presently preferred method of electron beam radiation or gamma-ray radiation being preferred. A package filled with nitrogen instead of air avoids tetracycline oxidation. Avoidance of light exposure and the addition of certain reductive agents, such as vitamin C, may further protect MPO1 from decomposition.

Most of the components of MPO1 are FDA approved safe agents, including tetracycline, Ethiodol and Onmipaque.

Chicken egg albumin is investigated as a drug-carrying material for oral and parental applications in several pharmacological labs. Either human or egg albumin may be used and is believed to be a safe material. No allergic reaction is observed. However, some individuals may be allergic to the egg albumin, especially given a history of food allergy to egg products. Most of these patients have only a temporary skin reaction, and very rarely experience asthma or serum sickness. The use of human serum albumin is believed to be a safer material and is preferred over egg albumin to make the multipurpose ointments.

The use of tetracycline as a sclerosing agent has long been established and is reconfirmed by the study discussed above. Without the tetracycline, MPOc has been observed to offer only a temporary embolization. This kind of temporary effect is often seen with biodegradable materials, such as Avitene which is a bovine collagen fiber. The zero recanalization rate as well as the ability to inhibit collateralization, are advantages features of the application of MPO1.

The process of MPO1 metabolization and organization is observed to be similar to the natural consequences of thrombosis. This makes MPO1 superior to the nondegradable materials used in the prior art with which chronic stimulation and inflammation may persist for years following use.

The dosage of MPO1 applied for clinical procedure can be less than 5 milliliters which would contain 250 milligrams of tetracycline. This amounts to only 25 percent of a one day dosage for antibacterial therapy, and at this low level, systemic side effects of tetracycline are minimal.

The leakage of MPO1 from an arteriovenous malformation to the lungs may occur clinically, although the animal study above did not show any significant leakage from the retes to the brain. However, MPO1 is clearly visible under X-ray and small amounts of leakage down to 0.02 milliliters can be easily detected during the embolization procedure. Once an unacceptable leakage, for example on the order of 0.4 milliliters occurs, the physician can stop the delivery of MPO1, embolize the large shunting fistula within the arteriovenous malformation with other devices, such as coils, and avoid further leakage from any further MPO1 embolization. Furthermore, the above study shows that up to 1.0 milliliter of MPO1 embolized to the lungs causes less than 5 percent of lung tissue loss. Such small losses are insignificant and are unlikely to have any clinical consequence.

A second embodiment involves the use of soft solid particles or multipurpose particles (MPP). Each member of the multipurpose ointment family discussed above can have a sister or corresponding particle-form product, which is derived from a modification in the preparation technique. Therefore, a series of sister products, MPP1 and so on, can be made according to the same principle in making the products in the family of MPOc. Like the multipurpose ointment, these flexible particles are soft and have excellent deformability, which allows easy access into the embolizing vascular beds or nidus, and which leads to a more complete embolization than using conventional particles. In addition, the MPP particles are radiopaque and easily visible under fluoroscopic monitoring. This opacity helps avoid pulmonary embolization and infarction, an iatrogenic or physician-induced complication of transcatheter embolization which may occur with radio-invisible material, such as polyvinyl alcohol particles. As in the case with other drug-carrier particles, MPP slowly releases their carried medicine at the site of embolization to reach the highest local effects without significant systemic disturbance.

The preparation of the sister products using MPP entails the same materials in using the corresponding MPOc products with the exception of changes in the mixing rates and modifiers. The emulsion again is made of an aqueous albumin solution with medications as may be needed and iodized oil injected into a hot Ethiodol solution through a fine needle at about 100 degrees centigrade. The inner diameter of the needle acts as a maximum particle-size grader. Liposoluble modifiers may be added to modify the particle surface. After a quick cooling, 1 to 5 times of the volume of ethanol is dissolved into the Ethiodol solution to dilute it. The particles can then be separated by filtration and suspended in liquid medium such as contrast medium solutions. The heating temperature, cooling speed and surface modifications can change the final deformability of these particles. The deformability of particles as well as their radiopaque visibility distinguishes MPP from other currently available embolic particles.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An endovascular embolic composition comprising:
   an aqueous solution of a matrix base for providing surface hydration when rendered insoluble; and
   a liquid oil base for providing self-lubrication mixed with said aqueous solution of said matrix base to form a semiliquid-semisolid soft dispersion of oil base in solidified matrix base for endovascular disposition for embolization of abnormal microvascular beds or nidi.

2. The embolic composition of claim 1 wherein said matrix base is comprised of albumin dissolved in an aqueous solution.

3. The embolic composition of claim 1 wherein said aqueous solution of said matrix base is mixed and emulsified with said liquid oil base in a volume ratio ranging between 1-to-1 to 1-to-5 respectively.

4. The embolic composition of claim 2 wherein said aqueous solution of said matrix base is mixed and dispersed in said liquid oil base in a volume ratio ranging between 1-to1 to 1-to-5 respectively.

5. The embolic composition of claim 3 wherein said liquid oil base is a ETHIODOL solution.

6. The embolic composition of claim 1 wherein said dispersion is heated in a water bath at a temperature of 50 degrees to 100 degrees centigrade to solidify the matrix base according to final physical characteristics of said embolic composition desired.

7. The embolic composition of claim 1 further comprising liposoluble modifiers.

8. The embolic composition of claim 1 further comprising water soluble modifiers.

9. The embolic composition of claim 1 further comprising stabilizing agents of said embolic composition.

10. The embolic composition of claim 1 wherein said modifiers and agents are selected from the grouping comprising surfacants, emulsifiers, water soluble polymers, stabilizing agents, cross-linking agents and combinations of the same for combination with said embolic composition.

11. The embolic composition of claim 1 further comprising radiopaque materials.

12. The embolic composition of claim 11 wherein said radiopaque materials are selected from the group comprising powders of metrizamide, tantalum, tungsten and combinations of the same.

13. The embolic composition of claim 1 further comprising medicants.

14. The embolic composition of claim 13 wherein said medicants are selected from the group comprising hemostatics, positive electrical charge donators, sclerosants, radioactive agents, chemotherapeutic agents and combinations of the same.

15. The embolic composition of claim 1 wherein said aqueous solution of said matrix base is mixed and dispersed in said liquid oil base in a volume ratio ranging between 1-to-1 to 1-to-5 respectively, wherein said liquid oil base is a ETHIODOL solution, wherein said emulsion is heated in a water bath at a temperature of 50 degrees to 100 degrees centigrade to solidify the matrix base according to final physical characteristics of said embolic composition desired, further comprises liposoluble modifiers, water soluble modifiers, stabilizing agents, radiopaque materials, and medicants for combination with said embolic composition.

16. The embolic agent of claim 1 wherein said aqueous solution of said matrix base and liquid oil base are emulsified and formed into particles of a predetermined size range, said particles then being suspended in a liquid medium for embolization.

17. The embolic composition of claim 1 wherein said aqueous solution of said matrix base and liquid oil base are formed into a homogeneous semiliquid-semisolid ointment for embolization.

* * * * *